(12) United States Patent
Sherwood et al.

(10) Patent No.: US 11,253,711 B2
(45) Date of Patent: Feb. 22, 2022

(54) IMPLANTABLE ENERGY STORAGE DEVICE INCLUDING A CONNECTION POST TO CONNECT MULTIPLE ELECTRODES

(71) Applicant: Cardiac Pacemakers, Inc., St. Paul, MN (US)

(72) Inventors: Gregory J. Sherwood, North Oaks, MN (US); Michael J. Root, Lino Lakes, MN (US); Eric Stemen, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 572 days.

(21) Appl. No.: 16/268,085

(22) Filed: Feb. 5, 2019

(65) Prior Publication Data

US 2019/0172653 A1 Jun. 6, 2019

Related U.S. Application Data

(63) Continuation of application No. 14/835,953, filed on Aug. 26, 2015, now Pat. No. 10,236,131, which is a
(Continued)

(51) Int. Cl.
*A61N 1/37* (2006.01)
*A61N 1/375* (2006.01)
(Continued)

(52) U.S. Cl.
CPC .............. *A61N 1/3754* (2013.01); *A61N 1/05* (2013.01); *A61N 1/375* (2013.01); *A61N 1/378* (2013.01);
(Continued)

(58) Field of Classification Search
CPC .......... A61N 1/05; A61N 1/375; A61N 1/378; A61N 1/3782; A61N 1/39; H01G 9/008;
(Continued)

(56) References Cited

U.S. PATENT DOCUMENTS 3,025,441 A 3/1962 West
3,331,759 A 7/1967 Middelhoek et al.
(Continued)

FOREIGN PATENT DOCUMENTS

EP 0877400 A1 11/1998
EP 1470267 B1 4/2009
(Continued)

OTHER PUBLICATIONS

US 8,503,164 B2, 08/2013, Sherwood et al. (withdrawn)
(Continued)

*Primary Examiner* — Amanda K Hulbert
(74) *Attorney, Agent, or Firm* — Schwegman Lundberg & Woessner, P.A.

(57) ABSTRACT

An example includes a capacitor case sealed to retain electrolyte, at least one anode disposed in the capacitor case, the at least one anode comprising a sintered portion disposed on a substrate, an anode conductor coupled to the substrate in electrical communication with the sintered portion, the anode conductor sealingly extending through the capacitor case to an anode terminal disposed on the exterior of the capacitor case with the anode terminal in electrical communication with the sintered portion, a second electrode disposed in the capacitor case, a separator disposed between the second electrode and the anode and a second electrode terminal disposed on an exterior of the capacitor case and in electrical communication with the second electrode, with the anode terminal and the second electrode terminal electrically isolated from one another.

15 Claims, 9 Drawing Sheets

Related U.S. Application Data continuation of application No. 12/968,536, filed on Dec. 15, 2010, now Pat. No. 9,123,470.

(60) Provisional application No. 61/288,072, filed on Dec. 18, 2009.

(51) Int. Cl.

| | |
|---|---|
| *H01G 9/052* | (2006.01) |
| *H01G 9/06* | (2006.01) |
| *A61N 1/378* | (2006.01) |
| *H01G 9/008* | (2006.01) |
| *H01G 9/04* | (2006.01) |
| *H01G 9/08* | (2006.01) |
| *H01G 9/10* | (2006.01) |
| *A61N 1/05* | (2006.01) |
| *H01G 9/035* | (2006.01) |

(52) U.S. Cl.
CPC ....... *A61N 1/3758* (2013.01); *A61N 1/37512* (2017.08); *H01G 9/008* (2013.01); *H01G 9/035* (2013.01); *H01G 9/04* (2013.01); *H01G 9/052* (2013.01); *H01G 9/06* (2013.01); *H01G 9/08* (2013.01); *H01G 9/10* (2013.01); *A61N 1/3782* (2013.01)

(58) Field of Classification Search
CPC .......... H01G 9/035; H01G 9/04; H01G 9/052; H01G 9/06; H01G 9/08; H01G 9/10; Y10T 29/417
See application file for complete search history.

(56) References Cited

U.S. PATENT DOCUMENTS

| | | |
|---|---|---|
| 3,445,731 A | 5/1969 | Saeki et al. |
| 3,627,520 A | 12/1971 | Rogers |
| 3,638,083 A | 1/1972 | Dornfeld et al. |
| 3,647,415 A | 3/1972 | Yano et al. |
| 4,059,116 A | 11/1977 | Adams |
| 4,085,397 A | 4/1978 | Yagher, Jr. |
| 4,107,762 A | 8/1978 | Shirn et al. |
| 4,406,286 A | 9/1983 | Stein |
| 4,720,767 A | 1/1988 | Chan et al. |
| 4,840,122 A | 6/1989 | Nerheim |
| 4,882,115 A | 11/1989 | Schmickl |
| 5,062,025 A | 10/1991 | Verhoeven et al. |
| 5,115,378 A | 5/1992 | Tsuchiya et al. |
| RE34,879 E | 3/1995 | Bocchi et al. |
| 5,468,254 A | 11/1995 | Hahn et al. |
| 5,591,211 A | 1/1997 | Meltzer |
| 5,591,217 A | 1/1997 | Barreras |
| 5,634,938 A | 6/1997 | Swanson et al. |
| 5,660,737 A | 8/1997 | Elias et al. |
| 5,763,911 A | 6/1998 | Matthews et al. |
| 5,807,397 A | 9/1998 | Barreras |
| 5,930,109 A | 7/1999 | Fishler |
| 6,115,235 A | 9/2000 | Naito |
| 6,141,205 A | 10/2000 | Nutzman et al. |
| 6,161,040 A | 12/2000 | Blunsden |
| 6,193,779 B1 | 2/2001 | Reichert et al. |
| 6,241,751 B1 | 6/2001 | Morgan et al. |
| 6,310,757 B1 | 10/2001 | Tuzuki et al. |
| 6,347,032 B2 | 2/2002 | Naito |
| 6,350,406 B1 | 2/2002 | Satou et al. |
| 6,351,371 B1 | 2/2002 | Yoshida et al. |
| 6,385,031 B1 | 5/2002 | Lerche et al. |
| 6,456,877 B1 | 9/2002 | Fishler |
| 6,459,566 B1 | 10/2002 | Casby et al. |
| 6,493,212 B1 | 12/2002 | Clarke et al. |
| 6,509,588 B1 | 1/2003 | O'Phelan et al. |
| 6,560,089 B2 | 5/2003 | Miltich et al. |
| 6,622,046 B2 | 9/2003 | Fraley et al. |
| 6,678,559 B1 | 1/2004 | Breyen et al. |
| 6,687,118 B1 | 2/2004 | O'Phelan et al. |
| 6,699,265 B1 | 3/2004 | O'Phelan et al. |
| 6,775,127 B2 | 8/2004 | Yoshida |
| 6,778,860 B2 | 8/2004 | Ostroff et al. |
| 6,785,123 B2 | 8/2004 | Keser |
| 6,801,424 B1 | 10/2004 | Nielsen et al. |
| 6,807,048 B1 | 10/2004 | Nielsen et al. |
| 6,850,405 B1 | 2/2005 | Mileham et al. |
| 6,855,234 B2 | 2/2005 | D'Astolfo, Jr. |
| 6,865,417 B2 | 3/2005 | Rissmann et al. |
| 6,914,769 B2 | 7/2005 | Welsch et al. |
| 6,952,608 B2 | 10/2005 | Ostroff |
| 6,954,670 B2 | 10/2005 | Ostroff |
| 7,024,246 B2 | 4/2006 | Acosta et al. |
| 7,072,713 B2 | 7/2006 | O'Phelan et al. |
| 7,327,557 B2 | 2/2008 | Poplett |
| 7,342,774 B2 | 3/2008 | Hossick-Schott et al. |
| 7,522,957 B2 | 4/2009 | Ostroff |
| 7,531,010 B1 | 5/2009 | Feger et al. |
| 7,564,677 B2 | 7/2009 | Poplett |
| 7,760,488 B2 | 7/2010 | Breznova et al. |
| 8,179,663 B2 | 5/2012 | Brabeck et al. |
| 8,619,408 B2 | 12/2013 | Sherwood et al. |
| 8,725,252 B2 | 5/2014 | Sherwood |
| 8,873,220 B2 | 10/2014 | Sherwood et al. |
| 8,988,859 B2 | 3/2015 | Sherwood et al. |
| 9,123,470 B2 | 9/2015 | Sherwood et al. |
| 9,129,749 B2 | 9/2015 | Sherwood et al. |
| 9,269,498 B2 | 2/2016 | Daley et al. |
| 9,424,997 B2 | 8/2016 | Sherwood et al. |
| 9,721,731 B2 | 8/2017 | Sherwood et al. |
| 10,096,429 B2 | 10/2018 | Sherwood et al. |
| 2003/0169560 A1 | 9/2003 | Welsch et al. |
| 2004/0019268 A1 | 1/2004 | Schmidt et al. |
| 2004/0147960 A1 | 7/2004 | O'Phelan et al. |
| 2004/0147961 A1 | 7/2004 | O'Phelan et al. |
| 2004/0240155 A1 | 12/2004 | Miltich et al. |
| 2005/0017888 A1 | 1/2005 | Sherwood et al. |
| 2006/0017089 A1 | 1/2006 | Taller et al. |
| 2006/0018083 A1 | 1/2006 | Schmidt |
| 2006/0035152 A1 | 2/2006 | Nishimura et al. |
| 2006/0139580 A1 | 6/2006 | Conner et al. |
| 2006/0139850 A1 | 6/2006 | Rorvick et al. |
| 2006/0166088 A1 | 7/2006 | Hokanson et al. |
| 2006/0174463 A1 | 8/2006 | O'Phelan et al. |
| 2006/0249774 A1 | 11/2006 | Sherwood |
| 2007/0109723 A1 | 5/2007 | Kuriyama et al. |
| 2007/0188980 A1 | 8/2007 | Hossick-Schott |
| 2008/0030927 A1 | 2/2008 | Sherwood |
| 2008/0170354 A1 | 7/2008 | Dvorak et al. |
| 2008/0198534 A1 | 8/2008 | Lee et al. |
| 2008/0208270 A1 | 8/2008 | Linder et al. |
| 2009/0231782 A1 | 9/2009 | Fujita et al. |
| 2009/0237862 A1 | 9/2009 | Nielsen et al. |
| 2009/0242415 A1 | 10/2009 | Yoshimitsu |
| 2009/0273884 A1 | 11/2009 | Shimizu et al. |
| 2010/0010562 A1 | 1/2010 | Daley et al. |
| 2010/0110614 A1 | 5/2010 | Umemoto et al. |
| 2010/0110615 A1 | 5/2010 | Nishimura et al. |
| 2010/0015751 A1 | 6/2010 | Miyachi et al. |
| 2010/0193731 A1 | 8/2010 | Lee et al. |
| 2010/0195261 A1 | 8/2010 | Sweeney et al. |
| 2010/0226066 A1 | 9/2010 | Sweeney et al. |
| 2010/0226070 A1 | 9/2010 | Yang et al. |
| 2011/0038098 A1 | 2/2011 | Taira et al. |
| 2011/0149474 A1 | 6/2011 | Sherwood et al. |
| 2011/0149475 A1 | 6/2011 | Sherwood et al. |
| 2011/0152958 A1 | 6/2011 | Sherwood et al. |
| 2011/0152959 A1 | 6/2011 | Sherwood |
| 2011/0152960 A1 | 6/2011 | Daley et al. |
| 2011/0152961 A1 | 6/2011 | Sherwood |
| 2013/0141842 A1 | 6/2013 | Sherwood et al. |
| 2015/0043130 A1 | 2/2015 | Sherwood et al. |
| 2015/0364264 A1 | 12/2015 | Sherwood et al. |

(56) References Cited

U.S. PATENT DOCUMENTS

| | | |
|---|---|---|
| 2016/0358715 A1 | 12/2016 | Sherwood et al. |
| 2017/0301476 A1 | 10/2017 | Sherwood et al. |

FOREIGN PATENT DOCUMENTS

| | | |
|---|---|---|
| JP | 2003522420 A | 7/2013 |
| WO | WO-2006139850 A1 | 6/2006 |
| WO | WO-2011075506 A2 | 6/2011 |
| WO | WO-2011075506 A3 | 6/2011 |
| WO | WO-2011075508 A2 | 6/2011 |
| WO | WO-2011075508 A3 | 6/2011 |
| WO | WO-2011075511 A2 | 6/2011 |
| WO | WO-2011075511 A3 | 6/2011 |

OTHER PUBLICATIONS

"U.S. Appl. No. 12/968,523, Advisory Action dated Sep. 22, 2014", 3 pgs.

"U.S. Appl. No. 12/968,523, Final Office Action dated Jun. 20, 2014", 7 pgs.

"U.S. Appl. No. 12/968,523, Non Final Office Action dated Jun. 21, 2013", 12 pgs.

"U.S. Appl. No. 12/968,523, Non Final Office Action dated Oct. 15, 2013", 9 pgs.

"U.S. Appl. No. 12/968,523, Non Final Office Action dated Dec. 5, 2014", 9 pgs.

"U.S. Appl. No. 12/968,523, Notice of Allowance dated Apr. 27, 2015", 5 pgs.

"U.S. Appl. No. 12/968,523, Response filed Jan. 8, 2014 to Non-Final Office Action dated Oct. 15, 2013", 11 pgs.

"U.S. Appl. No. 12/968,523, Response filed Mar. 6, 2015 to Non Final Office Action dated Dec. 5, 2014", 8 pgs.

"U.S. Appl. No. 12/968,523, Response filed Aug. 18, 2014 to Final Office Action dated Jun. 20, 2014", 7 pgs.

"U.S. Appl. No. 12/968,523, Response filed Sep. 23, 2013 to Non Final Office Action dated Jun. 21, 2013", 8 pgs.

"U.S. Appl. No. 12/968,536 , Response filed Sep. 23, 2013 to Non Final Office Action dated Jun. 21, 2013", 7 pgs.

"U.S. Appl. No. 12/968,536, Advisory Action dated Sep. 19, 2014", 3 pgs.

"U.S. Appl. No. 12/968,536, Final Office Action dated Jun. 19, 2014", 9 pgs.

"U.S. Appl. No. 12/968,536, Non Final Office Action dated Jan. 16, 2015", 9 pgs.

"U.S. Appl. No. 12/968,536, Non Final Office Action dated Jun. 21, 2013", 7 pgs.

"U.S. Appl. No. 12/968,536, Non Final Office Action dated Oct. 2, 2013", 17 pgs.

"U.S. Appl. No. 12/968,536, Notice of Allowance dated Apr. 28, 2015", 5 pgs.

"U.S. Appl. No. 12/968,536, Response filed Jan. 2, 2014 to Non-Final Office Action dated Oct. 2, 2013", 10 pgs.

"U.S. Appl. No. 12/968,536, Response filed Aug. 18, 2014 to Final Office Action dated Jun. 19, 2014", 8 pgs.

"U.S. Appl. No. 12/968,536, Response fled Apr. 16, 2015 to Non Final Office Action dated Jan. 16, 2015", 8 pgs.

"U.S. Appl. No. 12/968,555, Notice of Allowance dated Apr. 2, 2013", 9 pgs.

"U.S. Appl. No. 12/968,555, Notice of Allowance dated Aug. 28, 2013", 8 pgs.

"U.S. Appl. No. 12/968,555, Notice of Allowance dated Nov. 23, 2012", 9 pgs.

"U.S. Appl. No. 12/968,555, Response filed Oct. 29, 2012 to Restriction Requirement dated Sep. 27, 2012", 7 pgs.

"U.S. Appl. No. 12/968,555, Restriction Requirement dated Sep. 27, 2012", 7 pgs.

"U.S. Appl. No. 12/968,555, Supplemental Notice of Allowability dated Dec. 26, 2012", 2 pgs.

"U.S. Appl. No. 12/968,561, Non Final Office Action dated Jun. 30, 2015", 12 pgs.

"U.S. Appl. No. 12/968,561, Non Final Office Action dated Nov. 17, 2014", 8 pgs.

"U.S. Appl. No. 12/968,561, Notice of Allowance dated Oct. 19, 2015", 8 pgs.

"U.S. Appl. No. 12/968,561, Notice of Allowance dated Nov. 13, 2013", 11 pgs.

"U.S. Appl. No. 12/968,561, Response filed Feb. 12, 2015 to Non Final Office Action dated Nov. 17, 2014", 9 pgs.

"U.S. Appl. No. 12/968,561, Response filed Jul. 31, 2013 to Restriction Requirement dated Jun. 21, 2013", 7 pgs.

"U.S. Appl. No. 12/968,561, Response filed Sep. 30, 2013 to Restriction Requirement dated Aug. 29, 2013", 7 pgs.

"U.S. Appl. No. 12/968,561, Restriction Requirement dated Jun. 21, 2013", 6 pgs.

"U.S. Appl. No. 12/968,561, Restriction Requirement dated Aug. 29, 2013", 7 pgs.

"U.S. Appl. No. 12/968,571 , Response filed Apr. 3, 2013 to Non Final Office Action dated Nov. 9, 2012", 13 pgs.

"U.S. Appl. No. 12/968,571, Advisory Action dated Jun. 3, 2014", 3 pgs.

"U.S. Appl. No. 12/968,571, Advisory Action dated Aug. 22, 2013", 3 pgs.

"U.S. Appl. No. 12/968,571, Final Office Action dated Mar. 11, 2014", 15 pgs.

"U.S. Appl. No. 12/968,571, Final Office Action dated Jun. 3, 2013", 14 pgs.

"U.S. Appl. No. 12/968,571, Non Final Office Action dated Sep. 13, 2013", 15 pgs.

"U.S. Appl. No. 12/968,571, Non Final Office Action dated Nov. 9, 2012", 15 pgs.

"U.S. Appl. No. 12/968,571, Notice of Allowance dated Jun. 26, 2014", 7 pgs.

"U.S. Appl. No. 12/968,571, Response filed May 12, 2014 to Final Office Action dated Mar. 11, 2014", 9 pgs.

"U.S. Appl. No. 12/968,571, Response filed Jun. 10, 2014 to Final Office Action dated Mar. 11, 2014", 6 pgs.

"U.S. Appl. No. 12/968,571, Response filed Jul. 31, 2013 to Final Office Action dated Jun. 3, 2013", 11 pgs.

"U.S. Appl. No. 12/968,584 , Response filed Oct. 29, 2013 to Non Final Office Action dated Jul. 31, 2013", 10 pgs.

"U.S. Appl. No. 12/968,584, Non Final Office Action dated Jan. 30, 2013", 11 pgs.

"U.S. Appl. No. 12/968,584, Non Final Office Action dated Jul. 31, 2013", 12 pgs.

"U.S. Appl. No. 12/968,584, Notice of Allowance dated Dec. 27, 2013", 7 pgs.

"U.S. Appl. No. 12/968,584, Response filed Apr. 26, 2013 to Non Final Office Action dated Jan. 30, 2013", 10 pgs.

"U.S. Appl. No. 13/753,023, Non Final Office Action dated Jul. 24, 2014", 8 pgs.

"U.S. Appl. No. 13/753,023, Notice of Allowance dated Nov. 21, 2014", 7 pgs.

"U.S. Appl. No. 14/521,660, Final Office Action dated Feb. 4, 2016", 12 pgs.

"U.S. Appl. No. 14/521,660, Non Final Office Action dated Oct. 7, 2015", 20 pgs.

"U.S. Appl. No. 14/521,660, Notice of Allowance dated Apr. 20, 2016", 7 pgs.

"U.S. Appl. No. 14/521,660, Preliminary Amendment filed Nov. 18, 2014", 6 pgs.

"U.S. Appl. No. 14/521,660, Response filed Jan. 6, 2016 to Non Final Office Action dated Oct. 7, 2015", 8 pgs.

"U.S. Appl. No. 14/521,669, Response filed Mar. 31, 2016 to Final Office Action dated Feb. 4, 2016", 7 pgs.

"U.S. Appl. No. 14/835,953, Non Final Office Action dated Jun. 25, 2018", 7 pgs.

"U.S. Appl. No. 14/835,953, Notice of Allowance dated Nov. 6, 2018", 7 pgs.

"U.S. Appl. No. 14/835,953, Preliminary Amendment filed Oct. 1, 2015", 6 pgs.

(56) References Cited

OTHER PUBLICATIONS

"U.S. Appl. No. 14/835,953, Response filed May 7, 2018 to Restriction Requirement dated Mar. 8, 2018", 6 pgs.
"U.S. Appl. No. 14/835,953, Response filed Sep. 25, 2018 to Non Final Office Action dated Jun. 25, 2018", 8 pgs.
"U.S. Appl. No. 14/835,953, Restriction Requirement dated Mar. 8, 2018", 6 pgs.
"U.S. Appl. No. 15/238,400, Non Final Office Action dated Dec. 15, 2016", 14 pgs.
"U.S. Appl. No. 15/238,400, Notice of Allowance dated Mar. 27, 2017", 7 pgs.
"U.S. Appl. No. 15/238,400, Response filed Mar. 13, 2017 to Non Final Office Action dated Dec. 15, 2016", 7 pgs.
"U.S. Appl. No. 15/636,966, Non Final Office Action dated Jan. 26, 2018", 18 pgs.
"U.S. Appl. No. 15/636,966, Notice of Allowance dated Jun. 6, 2018", 7 pgs.
"U.S. Appl. No. 15/636,966, Preliminary Amendment filed Jun. 30, 2017", 4 pgs.
"U.S. Appl. No. 15/636,966, Response to Non Final Office Action dated Jan. 26, 2018", 6 pgs.
"U.S. Appl. No. 12/968,571, Preliminary Amendment filed Oct. 6, 2016", 5 pgs.
"U.S. Appl. No. 13/753,023, Response filed Oct. 22, 2014 to Non Final Office Action dated Jul. 24, 2014", 8 pgs.
"European Application Serial No. 10796246.6, Communication Pursuant to Rule 164(2)(a) EPC dated Dec. 6, 2017", 10 pgs.
"International Application Serial No. PCT/US2010/060432, Corrected International Preliminary Report on Patentability dated May 11, 2012", 22 pgs.
"International Application Serial No. PCT/US2010/060432, International Preliminary Report on Patentability dated Apr. 27, 2012", 16 pgs.
"International Application Serial No. PCT/US2010/060432, Invitation to Pay Additional Fees dated Sep. 13, 2011", 9 pgs.
"International Application Serial No. PCT/US2010/060432, Search Report dated Dec. 5, 2011", 6 pgs.
"International Application Serial No. PCT/US2010/060432, Written Opinion dated Dec. 5, 2011", 14 pgs.
"International Application Serial No. PCT/US2010/060437, International Preliminary Report on Patentability dated Jun. 28, 2012", 7 pgs.
"International Application Serial No. PCT/US2010/060437, Search Report dated Sep. 13, 2011", 4 pgs.
"International Application Serial No. PCT/US2010/060437, Written Opinion dated Sep. 13, 2011", 6 pgs.
"International Application Serial No. PCT/US2010/060444, International Preliminary Report on Patentability dated Jun. 28, 2012", 8 pgs.
"International Application Serial No. PCT/US2010/060444, International Search Report dated Sep. 14, 2011", 4 pgs.
"International Application Serial No. PCT/US2011/060444, Written Opinion dated Sep. 14, 2011", 7 pgs.
"Japanese Application Serial No. 2012-544737, Office Action dated Nov. 5, 2013", With English Translation, 6 pgs.
Bocek, Joseph M, et al., "Method and Apparatus for Charging Partitioned Capacitors", U.S. Appl. No. 11/462,301 filed Aug. 3, 2006, 53 pgs.
U.S. Appl. No. 12/968,523, U.S. Pat. No. 9,129,749, filed Dec. 15, 2010, Sintered Electrodes to Store Energy in an Implantable Medical Device.
U.S. Appl. No. 12/968,536, U.S. Pat. No. 9,123,470, filed Dec. 15, 2010, An Implantable Energy Storage Device Including a Connection Post to Connect Multiple Electodes.
U.S. Appl. No. 14/835,953, filed Aug. 26, 2015, An Implantable Energy Storage Device Including a Connection Post to Connect Multiple Electrodes.
U.S. Appl. No. 12/968,555, U.S. Pat. No. 8,619,408, filed Dec. 15, 2010, Sintered Capacitor Electrode Including a Folded Connection.
U.S. Appl. No. 13/753,023, U.S. Pat. No. 8,988,859, filed Jan. 29, 2013, Sintered Capacitor Electrode Including a Folded Connection.
U.S. Appl. No. 12/968,561, U.S. Pat. No. 9,269,498, filed Dec. 15, 2010, Sintered Capacitor Electode Including Multiple Thickness.
U.S. Appl. No. 12/968,571, U.S. Pat. No. 8,873,220, filed Dec. 15, 2010, Systems and Methods to Connect Sintered Aluminum Electodes of an Energy Storage Device.
U.S. Appl. No. 14/521,660, U.S. Pat. No. 9,424,997, filed Oct. 23, 2014, Systems and Methods to Connect Sintered Aluminum Electodes of an Energy Storage Device.
U.S. Appl. No. 15/238,400, U.S. Pat. No. 9,721,731, filed Aug. 16, 2016, Systems and Methods to Connect Sintered Aluminum Electodes of an Energy Storage Device.
U.S. Appl. No. 15/636,966, U.S. Pat. No. 10,069,429, filed Jun. 29, 2017, Systems and Methods to Connect Sintered Aluminum Electodes of an Energy Storage Device.
U.S. Appl. No. 12/968,584, U.S. Pat. No. 8,752,252, filed Dec. 15, 2010, Electric Energy Storage Including an Overcurrent Protector.

IMPLANTABLE ENERGY STORAGE DEVICE INCLUDING A CONNECTION POST TO CONNECT MULTIPLE ELECTRODES

CROSS-REFERENCE TO RELATED APPLICATIONS

This application is a continuation of U.S. application Ser. No. 14/835,953, filed Aug. 26, 2015, which is a continuation of U.S. application Ser. No. 12/968,536, filed Dec. 15, 2010, now issued as U.S. Pat. No. 9,123,470, which claims the benefit of U.S. Provisional Application No. 61/288,072, filed on Dec. 18, 2009, under 35 U.S.C. § 119(e), each of which is incorporated herein by reference in its entirety.

TECHNICAL FIELD

This document relates generally to energy storage and particularly to sintered electrodes to store energy in an implantable medical device.

BACKGROUND

Anodes and cathodes are the current collectors in energy storage devices. These current collectors are often designed to be very thin or brittle. Interconnecting thin or brittle subcomponents using a high-volume process is challenging because the current collectors can bend or break, which can cause malfunction of the energy storage device. In capacitors, some interconnection devices or methods lower the equivalent series resistance of the capacitor. Therefore, any improvements to interconnection devices and processes can increase yield and can also improve performance of the energy storage device.

SUMMARY

This document provides apparatus and methods for an energy storage device including a post connector to couple electrodes. An apparatus embodiment includes a capacitor case sealed to retain electrolyte, a first electrode disposed in the capacitor case, the first electrode comprising a substrate with a sintered portion on a side of the substrate, the sintered portion bordering a connection portion on the side of the substrate, the connection portion substantially free of sintering, an connection post pierced through the substrate at the connection portion and a first electrode terminal disposed on the exterior of the capacitor case in electrical communication with the connection post and the first electrode. In an embodiment, the apparatus includes a second electrode disposed in the capacitor case, a separator disposed between the second electrode and a first electrode, and a second electrode terminal disposed on an exterior of the capacitor case and in electrical communication with the second electrode, with the first electrode terminal and the second electrode terminal electrically isolated from one another.

One aspect of this disclosure provides a method for making a capacitor. According to an embodiment of the method, material is sintered onto a substrate of an electrode. In an embodiment, the substrate is free of sintered material sintered near a connection portion of the electrode. The electrode is stacked onto a connection post, a separator is stacked onto the connection post, and a second electrode is stacked onto the connection post. The stack is disposed in a capacitor case and the electrodes and the connection post are coupled to terminals. The capacitor case is filled with electrolyte and the case is sealed. Additionally, systems including the apparatus are provided.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
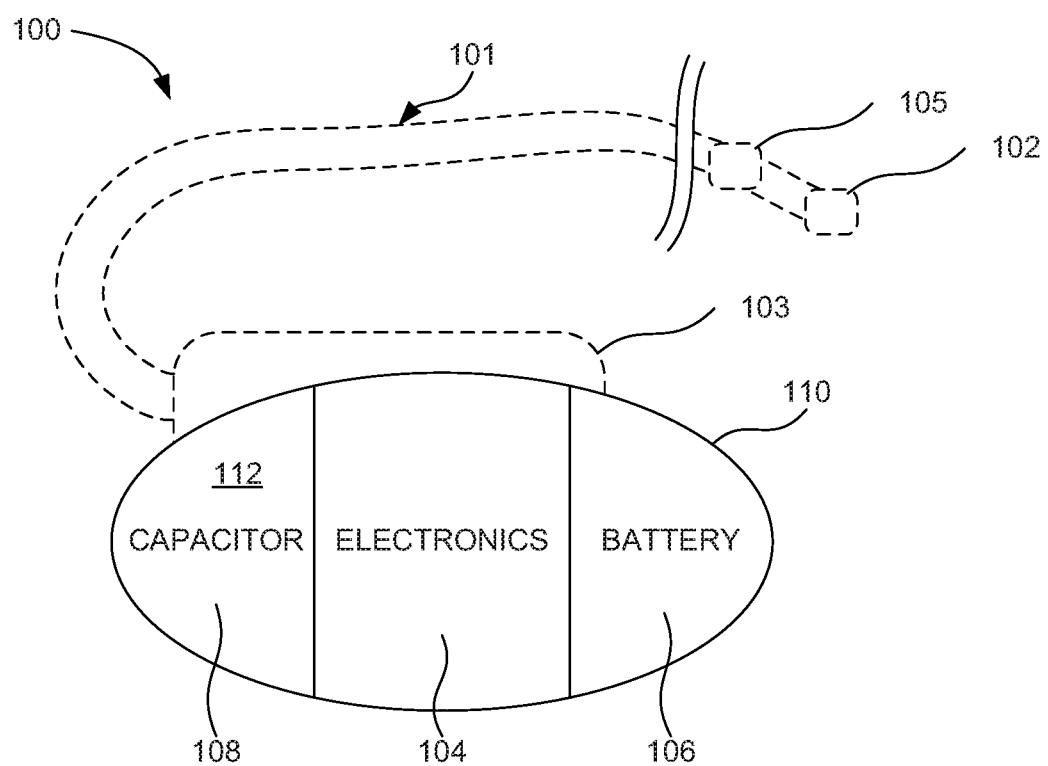
FIG. 1 is a schematic of a medical system including a sintered capacitor, according to some embodiments.

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This application is for sintered electrodes in an electrical energy storage device. Specific examples include sintered anodes formed of aluminum or its alloys. Certain examples are for use in aluminum electrolytic capacitors. Examples include electrodes with a sintered portion disposed onto at least one side of a substrate. Some examples include a stack of electrodes in which the substrates of multiple electrodes are interconnected. This interconnection method improves upon energy storage devices using etched electrodes because the foils may be bent together for interconnection without a low risk of breakage, whereas etched materials often break.

Sintering results in many interstices (i.e., spaces) between grains of the electrode improving energy density in part because of increased surface area. Sintered electrodes resemble crushed grains with interstices between the grains when viewed at a microscopic magnification. The interstices are filled with electrolyte, thereby increasing capacitance per unit of volume, as capacitance is proportional to a surface area exposed to electrolyte. An electrode with such interstices offers improved lateral or parallel movement of electrons in relation to a major surface of a flat electrode layer, as etched electrodes restrict lateral movement because the etchings result in voids that are typically perpendicular to the major surface of the flat layer. Accordingly, some examples have a lower ESR (equivalent series resistance) compared to etched foils due to this enhanced ionic flow.

Overall, an energy storage device using the sintered electrodes described here is well suited for use in an implantable medical device such as a defibrillator. Because sintering can produce a variety of shapes, sintered electrodes can be used to create energy storage devices such as capacitors that have custom shapes versus simple cylinders or a prism having a parallelogram as its base. Further, manufacturing efficiency is improved, such as by allowing electrodes to be nested on a web before they are excised from the web and stacked into a capacitor. In other words, nesting reduces waste by allowing more of the web to be converted into electrodes. The interstices are very small, making the electrodes rigid and able to withstand handling by a machine or assembly personnel. These electrodes demonstrate an improved energy density over etched electrodes and are therefore useful to make smaller implantable devices that are able to deliver an amount of energy required for a particular therapy.

FIG. 1 is a schematic of a medical system 100 including a sintered capacitor, according to some embodiments. The medical system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

Electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. The electronics 104 can be powered wirelessly using an inductor. Alternatively, the electronics 104 can be powered by a battery 106.

In some examples, electronics 104 are to direct small therapeutic bursts of energy to a patient from the battery 106.

For therapies that use energy discharge rates exceeding what battery 106 is able to provide, such as defibrillation, a capacitor 108 is used. Energy from the battery 106 is controlled by the electronics 104 to charge the capacitor 108. The capacitor 108 is controlled with the electronics 104 to discharge to a patient to treat the patient. In some examples, the capacitor 108 completely discharges to a patient, and in additional examples is switched on to provide therapeutic energy and switched off to truncate therapy delivery.

Some examples of a medical system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101 and are leadless. Leadless examples can be positioned in contact with the tissue to be stimulated, or can be positioned proximal to the tissue to shock the tissue to be stimulated through intermediary tissue. Leadless examples can be easier to implant and can be less expensive as they do not require the additional lead components. The housing 110 can be used as an electrode in leadless configurations.

In certain embodiments, the electronics 104 include an electronic cardiac rhythm management circuit coupled to the battery 106 and the capacitor 108 to discharge the capacitor 108 to provide a therapeutic defibrillation pulse. In some examples, the system 100 includes an anode and a cathode sized to deliver a defibrillation pulse of at least approximately 50 joules. Other configurations can deliver larger amounts of energy. Some configurations deliver less energy. In some examples, the energy level is predetermined to achieve a delivered energy level mandated by a governing body or standard associated with a geographic region, such as a European country. In an additional embodiment, the anode and cathode are sized to deliver a defibrillation pulse of at least approximately 60 joules. In some examples, this is the energy level is predetermined to achieve an energy level mandated by a governing body of another region, such as the United States. In some examples, electronics 104 are to control discharge of a defibrillation pulse so that the medical system 100 delivers only the energy mandated by the region in which the system 100 is used. In some examples, a pulse of 36 joules is delivered.

Packaging anodes and cathodes can reduce their efficiency. Interconnections between conductors coupled to electronics and to the electrodes of the capacitor 108 decrease efficiency, for example. Accordingly, anodes and cathodes are sized to compensate for decreases in efficiency. As such, in some embodiments, the capacitor 108 includes anodes and cathodes sized and packaged to deliver a defibrillation pulse of at least approximately 50 joules. Some are sized and packaged to deliver a defibrillation pulse of at least approximately 60 joules.

One characteristic of some sintered electrode examples is that at least one anode and a cathode have a DC capacitance that is approximately 23% greater than a AC capacitance for the at least one anode and the cathode of an etched capacitor that has 74.5 microfarads per cubic centimeter. In some examples, the at least one anode and the cathode have an AC capacitance of at least 96.7 microfarads per cubic centimeter at 445 total voltage. In some examples, this is comparable to an operating voltage of about 415 volts. This is a 30% improvement over an etched capacitor that has 74.5 microfarads per cubic centimeter. Total voltage is the voltage that allows 1 milliamp of leakage per square centimeter. Some examples are aged to 415 volts.

In certain examples, the capacitor 108 includes a capacitor case 112 sealed to retain electrolyte. In some examples, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal. Several materials can be used to form case 112, including, but not limited to, aluminum, titanium, stainless steel, nickel, a polymeric material, or combinations of these materials. The case 112 is sealed to retain electrolyte. Various electrolytes can be used including, but not limited to, Suzuki-Techno Corporation electrolyte model 1184. The case 112 includes a seal, such as a resin based seal including but not limited to epoxy, in some examples. Some examples include a rubber seal to seal case portions to one another, or to seal subcomponents such as a feedthrough to one or more case portion. In some examples, case 112 is welded together from subcomponents. Some examples include a case that includes one or more backfill ports, but the present subject matter is not so limited.

A hermetically sealed device housing 110 is used to house components, such as the battery 106, the electronics 104, and the capacitor 108. Hermeticity is provided by welding components into the hermetically sealed device housing 110 in some examples. Other examples bond portions of the housing 110 together with an adhesive such as a resin-based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The capacitor 108 is improved by the present electrode technology in part because it can be made smaller and with less expense. The improvement provided by these electrodes is pertinent to any application where high-energy, high-voltage, or space-efficient capacitors are desirable, including, but not limited to capacitors used for photographic flash equipment. In other words, present subject matter extends to energy storage devices that benefit from high surface area sintered electrodes including, but not limited to, aluminum. The electrodes described here can be incorporated into cylindrical capacitors that are wound, in addition to stacked capacitors.

Figure 2:
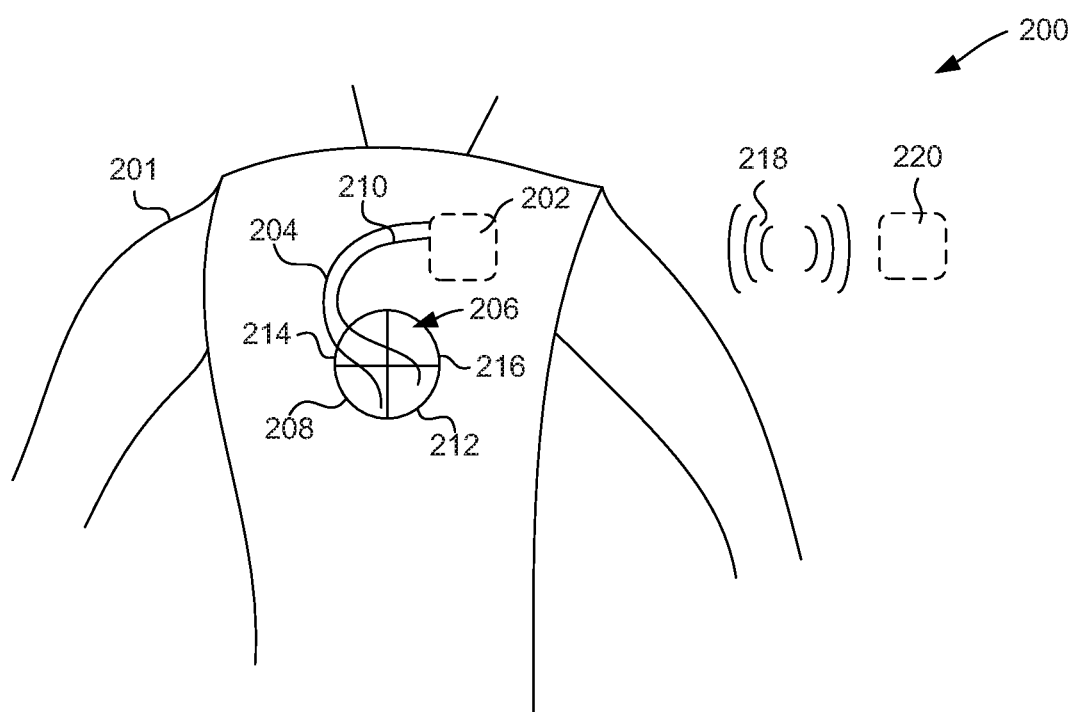
FIG. 2 is an implanted medical system including a sintered capacitor, according to some embodiments.

FIG. 2 is an implanted medical system 200, implanted in a patient 201, and including a sintered capacitor, according to some embodiments. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various embodiments, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both of those tissue regions. The second lead 210 is in direct contact with the right atrium 216 and the right ventricle 212 to sense and/or stimulate both of those tissue regions. The cardiac rhythm management device 202 uses the lead electrodes to deliver energy to the heart, between electrodes on the leads or between one or more lead electrodes and the cardiac rhythm management device 202. In some examples, the cardiac rhythm management device 202 is programmable and wirelessly communicates 218 programming information with a programmer 220. In some examples, the programmer 220 wirelessly 218 charges an energy storage device of the cardiac rhythm management device 202.

Figure 3A:
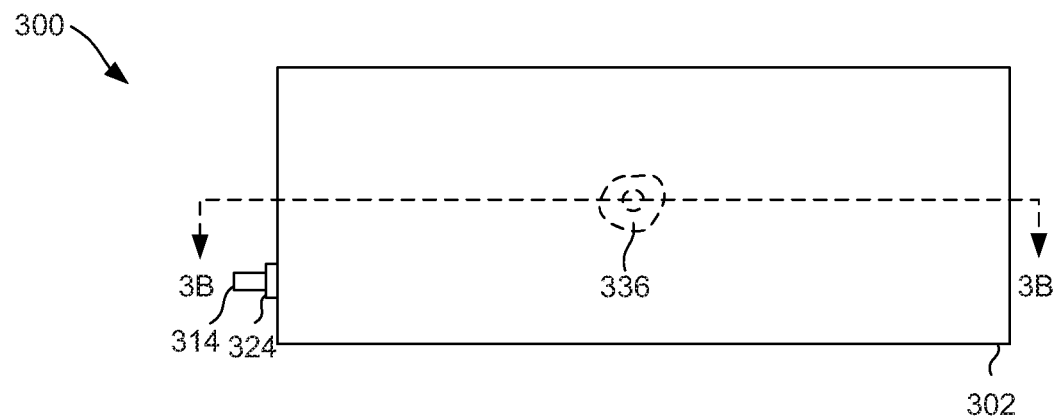
FIG. 3A is a plan view of a capacitor showing a connection post shown in hidden lines, according to various embodiments.
Figure 3B:
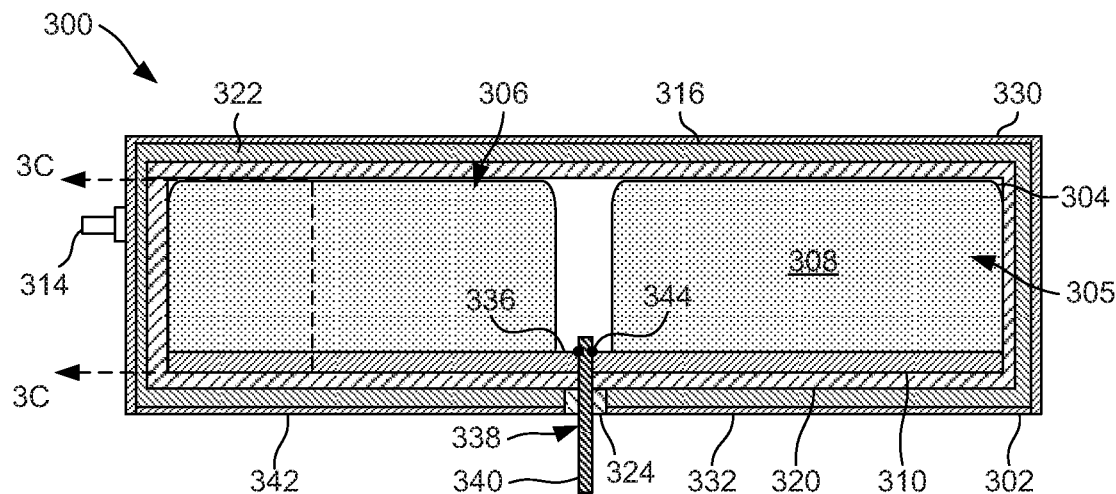
FIG. 3B is a cross section taken along line 3B-3B in FIG. 3A.
Figure 3C:
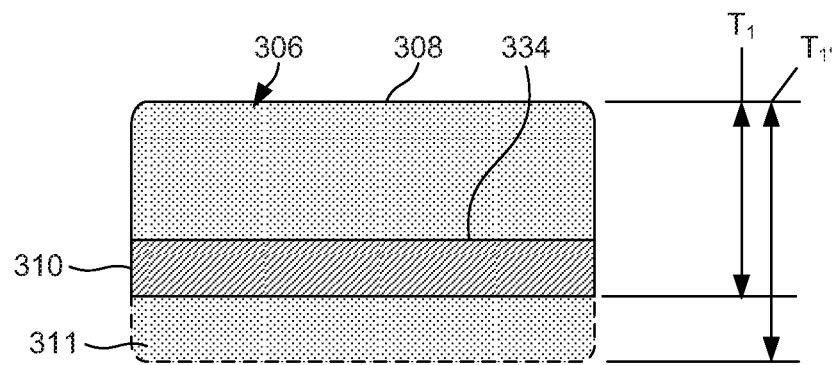
FIG. 3C is a cross section taken along line 3C-3C in FIG. 3B.

FIG. 3A is a plan view of a capacitor showing an connection post shown in hidden lines, according to various embodiments, FIG. 3B is a cross section taken along line 3B-3B in FIG. 3A. FIG. 3C is a cross section taken along line 3C-3C in FIG. 3B. Various embodiments include a capacitor case 302, In various examples, the capacitor case 302 is sealed to retain electrolyte. Examples of seals include welds, gasketed seals such as those using o-rings, adhesives and other seals. In some examples the capacitor case 302 includes a dish portion 330 and a lid portion 332.

Various embodiments include a first electrode 306 disposed in the capacitor case 302. In some embodiments, the first electrode 306 include a material 308 disposed on a substrate 310. In some examples, the material 308 includes sintered material. Some examples use a material 308 formed of sintered aluminum. In some examples, the material 308 is sintered onto the substrate 310. Optionally, a second sintered material 311 may be disposed on a second side of the substrate 310 in addition to the sintered material 308 disposed on a first side of the substrate 310. In some embodiments, the thickness of the sintered material 308 is substantially the same as the thickness of the second sintered material 311. In some embodiments, the thickness of the sintered material 308 is different from the thickness of the second sintered material 311. It is understood that electrodes described herein with sintered material disposed on one side of a substrate may also be configured with a substrate having sintered material disposed on two sides of the substrate without departing from the scope of the present subject matter.

Some examples include a portion 305 of the material 308 on a side 334 of the substrate 310, the portion 305 bordering a connection portion 336 of the substrate on the side of the substrate. In various embodiments, the connection portion 336 is substantially free of material such as sintered material. In various embodiments, the material 308 surrounds the connection portion 336. In some examples, the material 308 encircles the connection portion.

In some examples, the electrode 306 is an anode. In further embodiments, the electrode 306 is a cathode. In various embodiments, the electrode 306 is from around 300 micrometers to around 400 micrometers in thickness $T_1$, (optionally $T_1$.), but the present subject matter is not so limited.

Various embodiments include an connection post 338 pierced through the substrate 310. In some examples, the connection post 338 is pierced through the substrate 310 at the connection portion 336. Some examples include a first electrode terminal disposed on the exterior of the capacitor case in electrical communication with the connection post and the first electrode. The connection post 338 is shown as a cylinder having a circular cross section, but the present subject matter is not so limited and extends to other shapes, such as blades.

The connection post 338 and the substrate 310 are physically coupled using one or more of a variety of physical couplings including interference fit and clearance fit. In some examples, the substrate 310 is pierced by the connection post, causing an interference fit. In some examples, a joint 344 couples the connection post to the substrate 310. Various joints are contemplated including, but not limited to, welds, adhesives and mechanical deformations such as crimps.

The connection post 338 and the substrate 310 are electrically coupled using one or more of a variety of couplings including welds, crimps, conductive adhesives, jumpers, conductors, interconnection bars and other coupling means. Welds contemplated include laser welds and resistance welds. In various examples, a connection post 338 is disposed through a substrate 310 and then welded to the substrate, such as by laser welding or resistance welding. Optional embodiments add filler material during the welding process. The present subject matter extends to embodiments in which a weld filler material is disposed on the substrate to melt and weld the connection post 338 to the substrate 310. In some of these embodiments the weld filler material is a sintered material.

In various embodiments, the connection post 338 includes a terminal 340 disposed on an exterior 342 of the capacitor 300. Further wiling, connectors, wire harness and electronics are couplable to the terminal 340. In some embodiment, the connection post 338 is insulated from other components such as, but not limited to, other electrodes and the case 302, using an insulator 324.

Some examples include a second electrode 322 disposed in the capacitor case 302. In use, in some examples the second electrode 322 is of an opposite polarity from the first electrode 306. Various embodiments additionally include a separator 320 disposed between the second electrode 322 and a first electrode 306, Various embodiments include a second electrode terminal 314 disposed on an exterior 342 of the capacitor case 302 and in electrical communication with the second electrode 322. The first electrode terminal 340 and the second electrode terminal 314 are electrically isolated from one another.

Figure 4A:
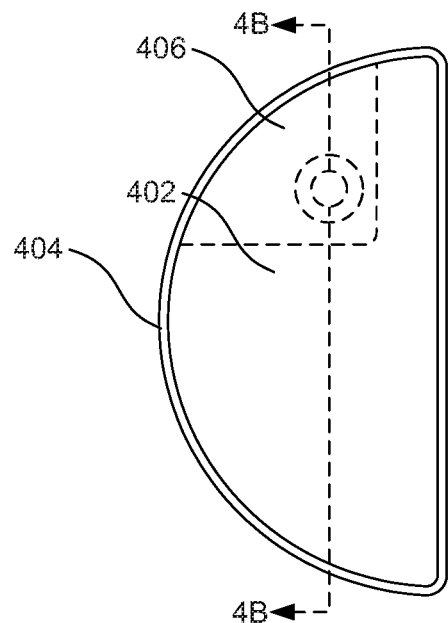
FIG. 4A is a plan view of capacitor electrodes with a connection post shown in hidden lines, according to various embodiments.
Figure 4B:
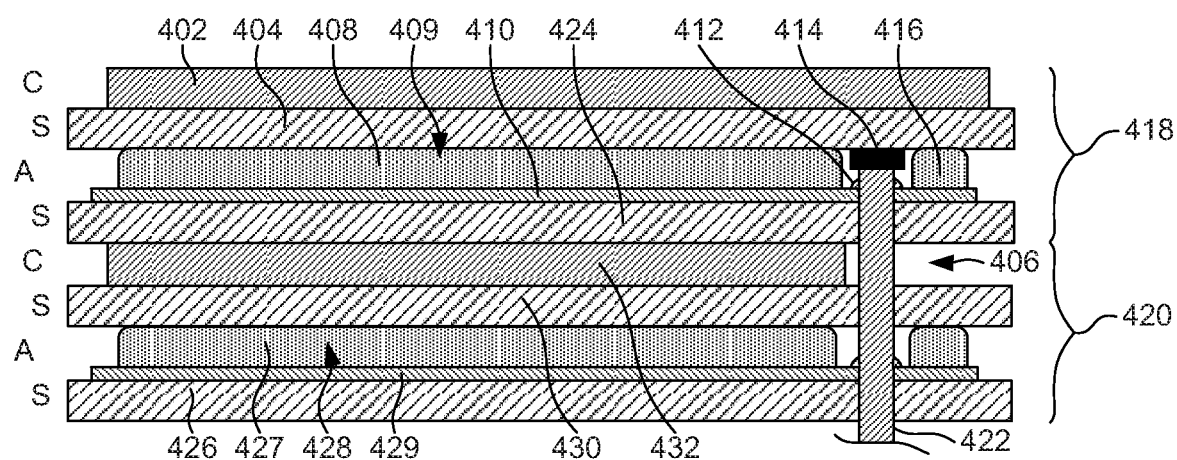
FIG. 4B is a cross section taken along line 4B-B in FIG. 4A.

FIG. 4A is a plan view of capacitor electrodes with an connection post shown in hidden lines, according to various embodiments. FIG. 4B is a cross section taken along line 4B-4B in FIG. 4A. In some examples, one or more electrodes are sheet or layer shaped. In some examples, the electrodes are stacked such that the stack has a generally rectangular envelope in a cross section, as depicted in FIG. 4B. In additional embodiments, the cross section envelope has flat top and bottom surfaces, with curvilinear or otherwise nonrectangular lateral edges. In various embodiments, when viewed in a top view such as in FIG. 4A, the stack has a custom shape such as a semicircle to better mate with a capacitor case.

In various embodiments, a series of electrodes, such as electrodes 402, 409, 432, 428, are disposed together in alignment with one another in a stack. In some examples, the electrodes 402 and 432 are cathodes, designated as "C" layers, electrodes 409 and 428 are anodic, designated as "A" layers, with separators 404, 424, 430 and 426 physically separating the anodes and cathodes from one another, and optionally from surrounding materials such as a capacitor case. In some examples, some of the electrodes include a material disposed on a substrate. For example, electrode 409 includes a material 408 disposed on a substrate 410.

Various embodiments include a second electrode 432, such as a cathode, that is sandwiched by a first separator 424 and a second separator 430. In some examples, the second electrode 432 and first separator 424 and second separator 430 are sandwiched by a first electrode 409 and a third electrode 428. In some examples, the third electrode 428 includes a second sintered portion 427 disposed on a second substrate portion 429. In some examples, the first substrate 410 and the second substrate 429 are sandwiched together.

In various embodiments, a connection post 422 is disposed through the electrodes 409 and 428 to electrically interconnect the electrodes 409 and 428. In some examples, the connection post 422 is physically coupled with one or more of the electrodes 409 and 428. For example, some configurations include a weld 412 that physically couples the connection post 422 to the electrode 409. In some examples, the weld is a laser weld. Additional configurations use other welds. In various embodiments, the electrode 432 includes a cut-out or void 406 to provide for passage of the connection post 422 through the electrode 432 without contacting the electrode 432. In additional examples, the cut-out is an aperture in the electrode 432. In various embodiments, connection post 422 is capped with an electrically insulative cap 414. In some examples, the electrically insulative cap 414 is sandwiched between the separator 404 and the connection post 422.

Figure 5A:
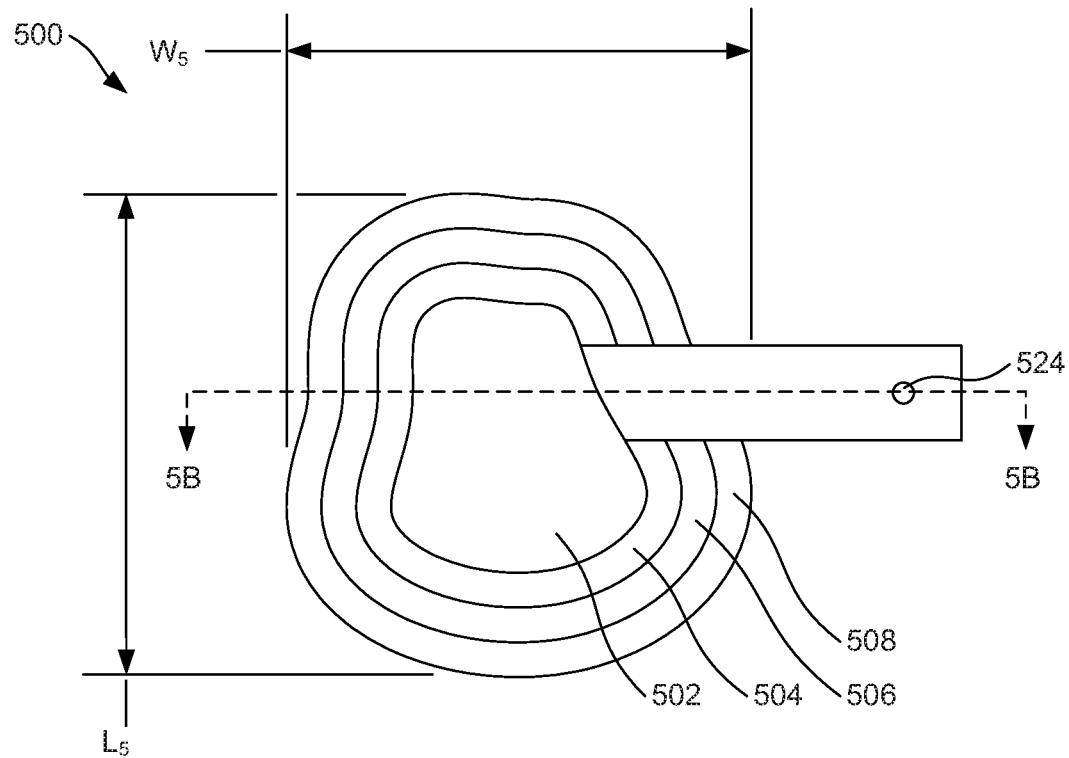
FIG. 5A is a plan view of capacitor electrodes having connection portions, according to various embodiments.
Figure 5B:
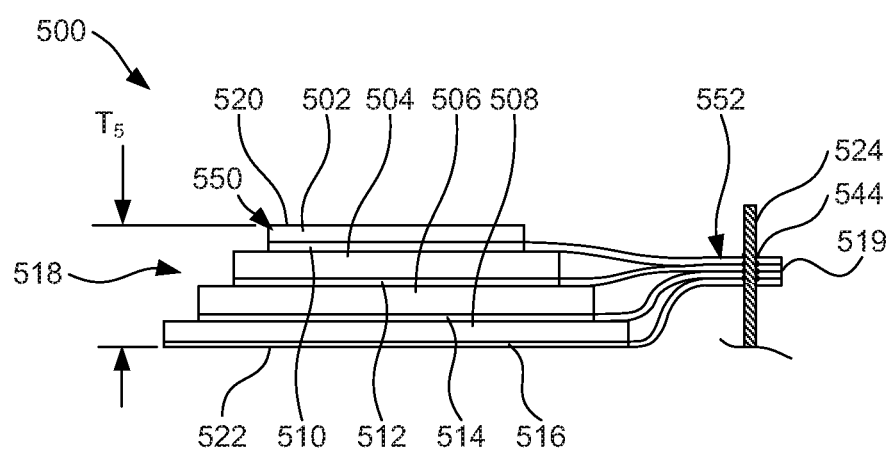
FIG. 5B is a cross section taken along line 5B-5B in FIG. 5A.

FIG. 5A is a plan view of capacitor electrodes having connection portions, according to various embodiments. FIG. 5B is a cross section taken along line 5B-5B in FIG. 5A. In some embodiments, the stack 500 is an anode. To increase surface area of an electrode, several electrodes are positioned against one another. In certain examples, each electrode includes one or more sintered portion disposed on a substrate. A first electrode includes a main portion, such as a sintered portion, 502 and a substrate 510. A second electrode includes a second main portion, such as a second sintered portion, 504 and a second substrate 512. A third electrode includes a third portion such as a third sintered portion 506 and a third substrate 514. A fourth electrode includes a fourth portion such as a fourth sintered portion 508 and a fourth substrate 516. The present subject matter is not limited to stacks of sintered material and extends to stacks of other materials, such as etched materials.

In various examples, the electrodes are interconnected to one another physically and electrically. A stack of first portions 550 defines a contoured side profile 518 in some examples. In certain embodiments, a stack of connection members 552 has a rectangular cross section. Embodiments in which both the first stack and the second stack have a rectangular cross section are possible. Additionally, some examples define a contoured side profile of each of a stack of first portions and a stack of connection members 552. In various embodiments, a connection post 524 pierces the stack of connection members 552 to electrically interconnect the connection members 552. In some embodiments, welds 554 physically connect the connection post 524 to respective connection members.

In some examples, the electrodes each abut one another and are electrically connected via the abutment. In some examples, the sintered portions are welded to one another using resistance welding, such as by applying a voltage across several electrodes along the axis of stacking. In some examples, substrates are interconnected to define an edge face 519. Along the edge face 519, interconnection configurations include, but are not limited to, welding (including, but not limited to, laser welding), adhesion fasteners, and combinations thereof. Additionally, the substrates can be resistance welded together such as by pinching and welding.

In the illustrated configuration, a first sintered portion 502 is sintered onto a first substrate 510, and a second sintered portion 504 is sintered onto a second substrate 512. The first substrate 510 faces the second sintered portion 504 and abuts it. In additional configurations, the second electrode is flipped, and the first substrate 510 abuts the second substrate 512.

In the illustrated configuration, the plurality of anodes are stacked to a stack height $T_5$, and at least two of the sintered anodes have respective widths, perpendicular to the height $T_5$, that are substantially different such that the plurality of sintered anodes define a side profile 518 including a contoured edge, with the contoured edge extending between a top major face 520 of a top sintered portion 502 and a bottom major face 522 of a bottom substrate 516. Various examples have an overall width $W_5$ perpendicular to the height $T_5$. In some examples at least two of the sintered anodes have respective lengths, perpendicular to the height $T_5$, that are substantially different such that the plurality of sintered anodes define a side profile 518 include a contoured edge, with the contoured edge extending between a top major face 520 of a top sintered portion 502 and a bottom major face 522 of a bottom substrate 516. Accordingly, the top major face 520 and the bottom major face 522 have different areas. The top major face 520 and the bottom major face 522 are substantially parallel. Various embodiments have an overall length $L_5$.

In another configuration, the plurality of electrodes are stacked to a stack height $T_5$, and at least two of the sintered anodes have respective widths, perpendicular to the height $T_5$, that are substantially equal such that the plurality of sintered anodes define a side surface that is substantially parallel to the height $T_5$. In the illustrated configuration, the top major face 520 and the bottom major face 522 are shaped similarly, but in additional embodiments, they are shaped differently.

Figure 6A:
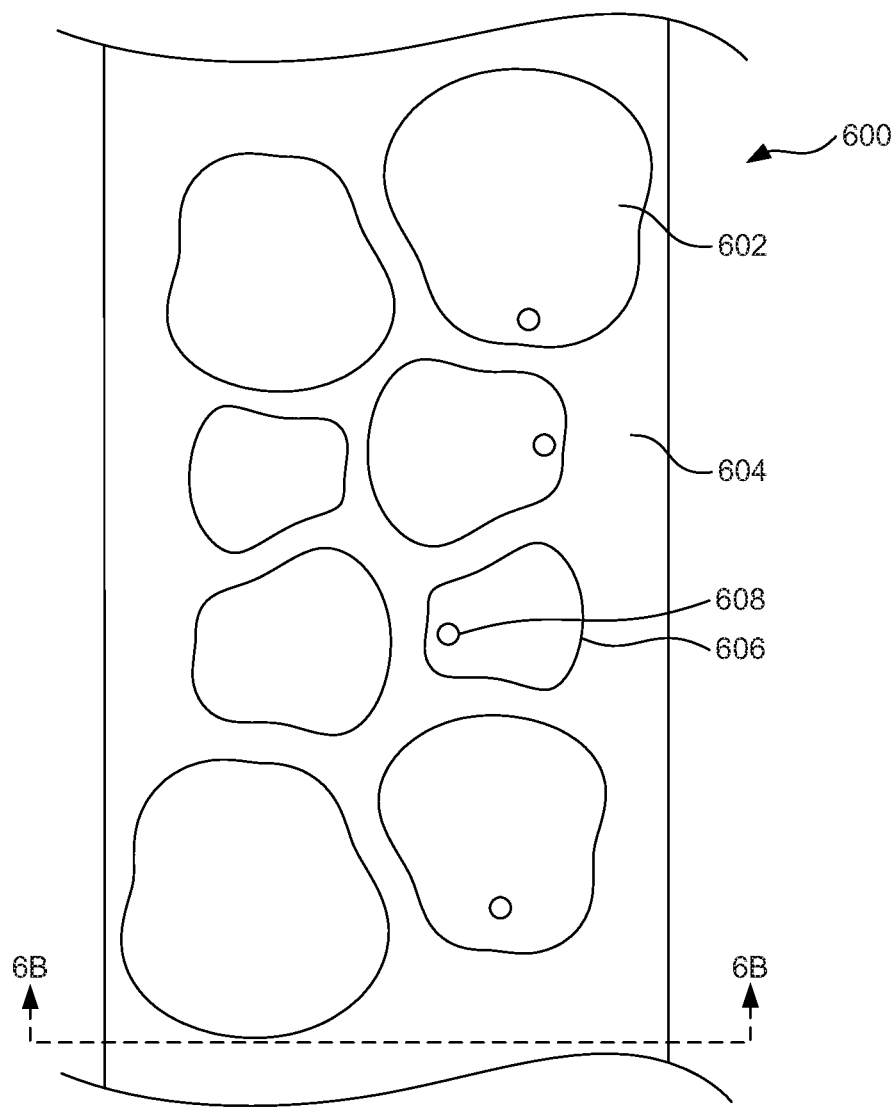
FIG. 6A is a plan view of a manufacturing web with nested sintered portions, according to various embodiments.
Figure 6B:
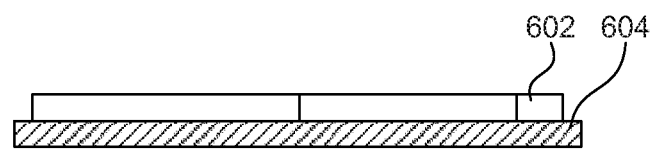
FIG. 6B is a cross section taken along the line 6B-6B in FIG. 6A.

FIG. 6A is a plan view of a manufacturing web with nested sintered portions, according to various embodiments. FIG. 6B is a cross section taken along the line 6B-6B in FIG. 6A. Electrodes 602 are sintered onto a substrate 604. In various embodiments, the sintered portions are excised from the web 600. In some examples, a slug is cut on the illustrated perimeters, around them, or inside them, depending on the process used. If foils are desired, such as for use as interconnects, one or more slugs are excised around the illustrated perimeters. If no foils are desired, one or more slugs can be excised substantially at the illustrated perimeters such as perimeter 606. In some embodiments, a process cuts the slugs, such as to provide a fresh cut surface or squared edges. FIG. 6B is a front view of the electrodes and substrate of FIG. 6A and illustrates that the slugs are of a common height. The present subject matter is not so limited. Various embodiments include connection portions such as connection portion 608 that are substantially free of sintered material. In various embodiments, the connection portions are to receive a connection post that pierces the substrate 604.

Figure 7A:
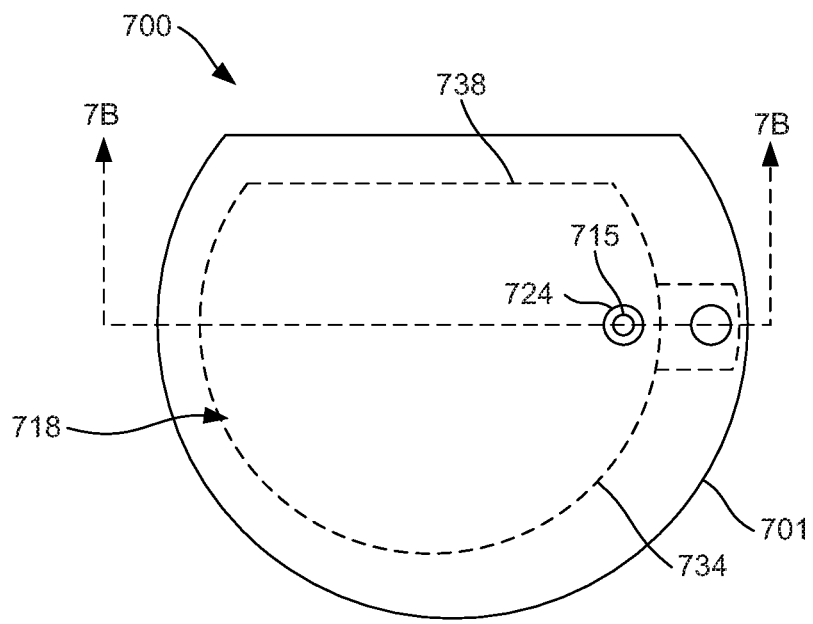
FIG. 7A is a plan view of a capacitor, according to various embodiments.
Figure 7B:
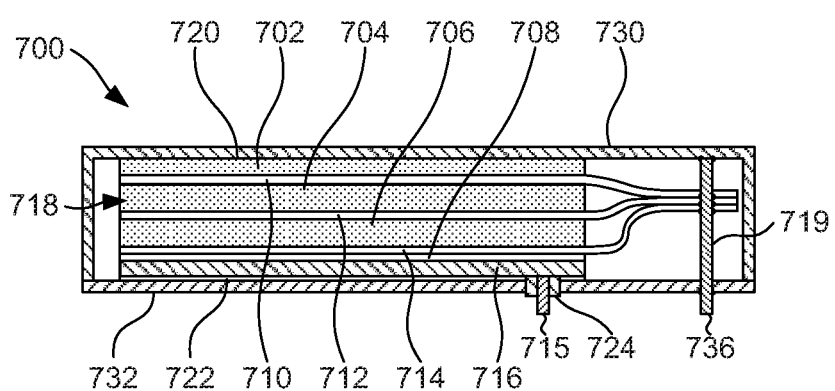
FIG. 7B is a cross section taken along the line 7B-7B in FIG. 7A. FIG.

FIG. 7A is a plan view of a capacitor, according to various embodiments. FIG. 7B is a cross section taken along the line 7B-7B in FIG. 7A. Various embodiments include a capacitor stack 718 disposed in a capacitor case 701. The capacitor case, in various embodiments, includes a dish shaped portion 730 and a lid 732, with the lid sealed to the dish shaped portion 730.

In various embodiments, the capacitor stack 718 includes a plurality of electrodes and separator. For example, a first separator 720 is disposed between the case 701 and a first electrode 702 to physically separate the electrode 702 from the case 701. In some examples, the stack 718 additionally includes a first electrode 702 including material disposed on a substrate 710. Some examples include a second electrode 704 including material disposed on a substrate 712. Some examples include a third electrode 706 including sintered material disposed on a substrate 714. In some examples, the first, second and third electrodes abut and are in electrical communication with one another. In additional examples, the first, second and third electrodes abut the capacitor case 701. In some examples, the first, second and third electrodes are anodic.

Various examples additionally include a further electrode 716. In various embodiments, one or more separators 708 separate the further electrode 716 from additional electrodes, such as the electrode including substrate 714. In additional embodiments, a separator 722 separates the further electrode 716 from the case 701 such as by separating the further electrode 716 from the lid 732.

In various embodiments, a connection post 719 is fixed to the capacitor case 701. In some examples, the connection post 719 is welded to a dish shaped portion 730 of the capacitor case 701. In various embodiments, the first, second and third electrodes are stacked into the dish shaped portion 730, and as they are stacked into the dish shaped portion, the connection post pierces connection members of the electrodes. Separator is stacked onto the third electrode, and a further electrode 716 is stacked into the dish shaped portion 730. In various embodiments, a lid 732 is fixed to the dish shaped portion, with a feedthrough including an electrical insulator 724 and a terminal 715 is disposed through the lid and placed into connection with the further electrode 716 such as by welding. In some examples, the further electrode 716 is welded to the feedthrough prior to fastening the lid 732 to the dish shaped portion 730. In various embodiments, after the lid 732 is fastened to the dish shaped portion 730, the connection post is welded to the lid 732, extending through the lid to define a terminal 736. In some examples, the first, second and third electrodes share a common polarity with the case 701.

In various examples, one or more of the substrates, such as substrate 710, defines an at least partially convex outer perimeter 734. In some examples, the perimeter 734 is completely convex. In some examples, the convex outer perimeter 734 is at least partially circular. In some examples, the perimeter is completely circular. In some examples, convex perimeter and a convex perimeter of the further electrode 716 are coextensive.

In various embodiments, the first, second and third electrodes are aligned to the case 701 via the connection post 719. In some examples, the first, second and third electrodes are aligned to the case 701 and the connection post 719, such as by dimensioning tolerances for each independently. In some examples, the first, second and third electrodes have a perimeter shape to be disposed in the case with the case to restrict rotation of the plurality of first electrodes around the connection post. For example, a chord 738 restricts rotation.

Figure 8:
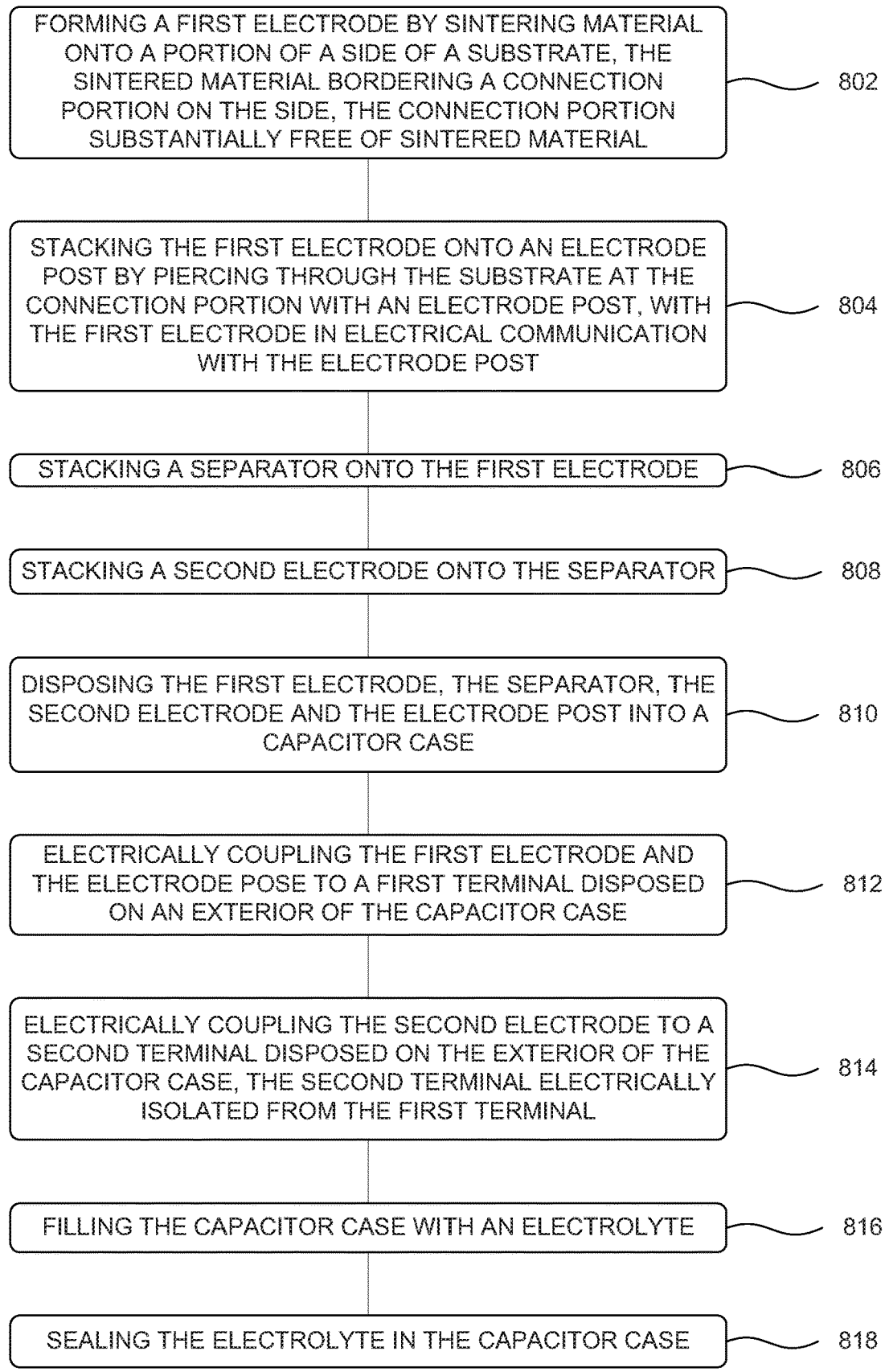
FIG. 8 is a method of making a capacitor, according to some embodiments.

FIG. 8 is a method of making a capacitor, according to some embodiments. At 802, the method includes forming a first electrode by sintering material onto a portion of a side of a substrate, the sintered material bordering a connection portion on the side, the connection portion substantially free of sintered material. At 804, the method includes stacking the first electrode onto an connection post by piercing through the substrate at the connection portion with an connection post, with the first electrode in electrical communication with the connection post. At 806, the method includes stacking a separator onto the first electrode. At 808, the method includes stacking a second electrode onto the separator. At 810, the method includes disposing the first electrode, the separator, the second electrode and the connection post into a capacitor case. At 812, the method includes electrically coupling the first electrode and the electrode pose to a first terminal disposed on an exterior of the capacitor case. At 814, the method includes electrically coupling the second electrode to a second terminal disposed on the exterior of the capacitor case, the second terminal electrically isolated from the first terminal. At 816, the method includes filling the capacitor case with an electrolyte. At 818, the method includes sealing the electrolyte in the capacitor case.

Some optional methods include sintering a plurality of sintered portions onto a web in a nested configuration, with at least a first sintered portion having a different area than a second sintered portion. Further optional methods include excising each of the sintered portions from the web by cutting the web around a plurality of sintered portions.

Figure 9A:
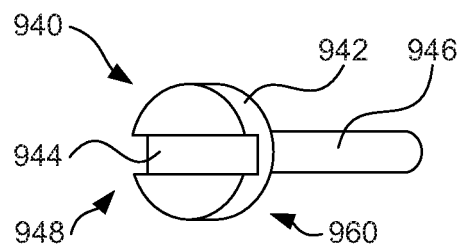
FIG. 9A is a perspective view of a connection post including a slotted base, according to some embodiments.
Figure 9B:
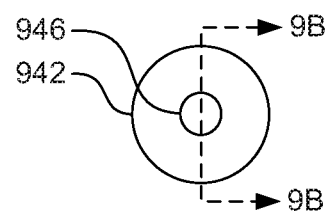
FIG. 9B is a side view of a slotted connection post according to some embodiments.
Figure 9C:
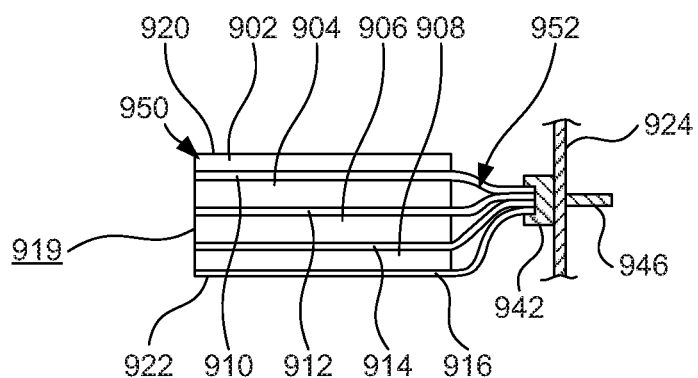
FIG. 9C is a schematic showing the slotted connection post of FIG. 9B sectioned along the line 9B-9B, and a capacitor stack, according to some embodiments.

FIG. 9A is a perspective view of a connection post including a slotted base, according to some embodiments. FIG. 9B is a side view of a slotted connection post according to some embodiments. FIG. 9C is a schematic showing the slotted connection post of FIG. 9B sectioned along the line 9B-9B, and a capacitor stack, according to some embodiments. A stack of electrodes 950 is anodic in some examples, and cathodic in other examples. To increase the effective surface area of one or more electrodes, several electrodes are positioned against one another and electrically interconnected to one another. In some examples, the electrodes each abut one another and are electrically connected via the abutment.

In certain examples, each electrode of the stack of electrodes 950 includes one or more sintered portions disposed on a substrate. A first electrode includes a main portion 902, such as a sintered portion, and a substrate 910. A second electrode includes a second main portion 904, such as a second sintered portion, and a second substrate 912. A third electrode includes a third portion 906 such as a third sintered portion and a third substrate 914. A fourth electrode includes a fourth portion 908 such as a fourth sintered portion and a fourth substrate 916. The present subject matter is not limited to stacks of sintered material and extends to stacks of other materials, such as etched materials.

In certain embodiments, one or more of the electrodes of the stack of electrodes 950 includes a connection member. In some examples, a connection member is formed from substrate of an electrode. In various embodiments, the connection members 952 are bunched into a stack and electrically interconnected. Various types of connections are possible, including welds, fasteners, rivets and other connections. A stack of connection members 952 has a rectangular cross section, in some embodiments.

A connection post 940 interconnects the connection members 952, and accordingly, the stack of electrodes 950, in some examples. The connection post 940 includes a base 942 defining a slot 944 and an elongate post 946 extending from the base 942. Although the base 942 and the post 946 are shown having different diameters, the present subject matter is not so limited, and includes examples in which the base and the post have the same form factor. In various examples, the post 946 extends through a device case 924, while the base 942 is coupled to connection members. The connection post 940 is cylindrical, but can also have another shape, such as a rectangular shape. In various examples, the connection post 940 defines a slot 944 extending from a first side 948 of the connection post 940 to a second side 960 of the connection post 940, which in some examples is opposite the first side 948.

The bunched or stacked connection members 952 are disposed in the slot 944 of the connection post 940. In some examples, the plurality of connection members is interconnected together before they are inserted in the slot 944. In additional embodiments, the plurality of connection members is first bunched, then inserted into the slot 944, and then physically interconnected together, such as by welding, after they are inserted in the slot 944. In the slot 944, the connection members are physically and electrically connected to the connection post 940. Types of connections include welds, fasteners, rivets and other connections. The connection post 940 is thicker than each of the connection members of the stack of connection members 952, in some examples. As such, the connection post 940 can endure higher welding energies without melting or damage.

In some examples, once the connection members 952 are coupled with the connection post 940, assembly becomes easier, as the post can be maneuvered through a hole or feedthrough in the device case 924. In some examples, maneuvering the connection post 940 is easier than maneuvering the connection members 952, at least because the connection members are easily damaged when handled individually. Accordingly, bunching the connection members 952 and coupling them into the slot 944 helps to protect them, and speeds manufacturing, in some embodiments.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An apparatus, comprising:
a capacitor case sealed to retain electrolyte;
a first electrode disposed in the capacitor case, the first electrode comprising a substrate with a sintered portion on a side of the substrate, the sintered portion bordering a connection portion on the side of the substrate, the connection portion substantially free of sintering;
a connection post connected to the substrate at the connection portion, wherein the connection post includes an elongate post that is pierced through the connection portion, and wherein the first electrode is aligned to the case via the connection post;
a first electrode terminal disposed on an exterior of the capacitor case in electrical communication with the connection post and the first electrode;
a second electrode disposed in the capacitor case;
a separator disposed between the second electrode and a first electrode; and
a second electrode terminal disposed on an exterior of the capacitor case and in electrical communication with the second electrode, with the first electrode terminal and the second electrode terminal electrically isolated from one another.

2. The apparatus of claim 1, wherein the first electrode has a perimeter shape to be disposed in the case with the case shaped to restrict rotation of the first electrode around the connection post.

3. The apparatus of claim 1, wherein the first electrode comprises a sheet with a main body comprising the sintered portion, and a connection member extending away from the main body comprising the connection portion.

4. The apparatus of claim 1, wherein the connection post is pierced through the substrate.

5. The apparatus of claim 4, wherein a second electrode is sandwiched by a first separator and a second separator, and the second electrode and first separator and second separator are sandwiched by the first electrode and a third electrode that includes a second substrate portion, with the substrate and the second substrate portion sandwiched together.

6. The apparatus of claim 1, wherein the case includes a dish portion and lid portion, with the connection post fixed to the dish portion and extending out of an interior of the dish portion.

7. The apparatus of claim 6, wherein the connection post extends through the lid.

8. The apparatus of claim 6, wherein the connection post is welded to the lid.

9. The apparatus of claim 1, wherein the sintered portion surrounds the connection portion.

10. A system, comprising:
a hermetically sealed device housing;
a battery disposed in the hermetically sealed device housing;
a capacitor disposed in the hermetically sealed device housing, the capacitor comprising:
a capacitor case sealed to retain electrolyte;
a first electrode disposed in the capacitor case; the first electrode comprising a substrate with a sintered portion on a side of the substrate, the sintered portion bordering a connection portion on the side of the substrate; the connection portion substantially free of sintering;
a connection post connected to the substrate at the connection portion; wherein the connection post includes an elongate post that is pierced through the connection portion, and wherein the first electrode is aligned to the case via the connection post;
a first electrode terminal disposed on an exterior of the capacitor case in electrical communication with the connection post and the first electrode;
a second electrode disposed in the capacitor case;
a separator disposed between the second electrode and a first electrode; and
a second electrode terminal disposed on an exterior of the capacitor case and in electrical communication with the second electrode, with the first electrode terminal and the second electrode terminal electrically isolated from one another; and
an electronic cardiac rhythm management circuit coupled to the battery and the capacitor and adapted to charge the capacitor with the battery and to discharge the capacitor to provide a therapeutic defibrillation pulse.

11. The system of claim 10, wherein the first electrode has a perimeter shape to be disposed in the case with the case shaped to restrict rotation of the first electrode around the connection post.

12. The system of claim 11, wherein the electronic cardiac rhythm management circuit comprises a defibrillator circuit.

13. The system of claim 12, wherein the first electrode is an anode, and the second electrode is a cathode, and the defibrillator circuit is to entirely discharge the anode and the cathode to provide a single therapeutically effective defibrillator pulse.

14. The system of claim 13, wherein the anode and the cathode are sized to deliver a defibrillation pulse of approximately 50 joules.

15. The system of claim 13, wherein the anode and the cathode are sized and packaged to deliver a defibrillation pulse of approximately 50 joules.

* * * * *